United States Patent [19]
Abildt et al.

[11] Patent Number: 4,461,641
[45] Date of Patent: Jul. 24, 1984

[54] HERBICIDAL MIXTURES

[75] Inventors: Uwe Abildt, Grenzach-Wyhlen, Fed. Rep. of Germany; Theodor Langauer, Muttenz, Switzerland

[73] Assignee: Ciba-Geigy Corporation, Ardsley, N.Y.

[21] Appl. No.: 352,437

[22] Filed: Feb. 25, 1982

[51] Int. Cl.$^3$ ..................... A01N 25/02; A01N 25/00
[52] U.S. Cl. .......................................... 71/93; 71/118; 71/DIG. 1
[58] Field of Search ...................... 71/93, 118, DIG. 1

[56] References Cited

U.S. PATENT DOCUMENTS

| | | | |
|---|---|---|---|
| 3,948,636 | 4/1976 | Marks | 71/112 |
| 4,313,847 | 2/1982 | Chasin et al. | 71/118 X |
| 4,371,390 | 2/1983 | Le Clair et al. | 71/93 |
| 4,372,777 | 2/1983 | Le Clair et al. | 71/93 |

FOREIGN PATENT DOCUMENTS

| | | |
|---|---|---|
| 2328340 | 12/1973 | Fed. Rep. of Germany . |
| 167029 | 2/1975 | Hungary . |
| 1421092 | 1/1967 | United Kingdom . |
| 1302720 | 1/1973 | United Kingdom . |

Primary Examiner—Catherine L. Mills
Attorney, Agent, or Firm—Frederick H. Rabin; Bruce M. Collins

[57] ABSTRACT

Flowable herbicidal compositions which contain an active component combination of at least one chlorotriazine and a chloroacetanilide form stable aqueous dispersions if the surfactant component of the composition consists of an anionic surfactant from the series of the mono- or diphosphoric acid esters of phenol polyglycol ethers and a mixture of two non-ionic surfactants from the series of the alkoxy, alkanoyloxy or phenol polyglycol ethers which differ by at least one glycol unit.

4 Claims, No Drawings

HERBICIDAL MIXTURES

The present invention relates to a flowable herbicidal composition in the form of an aqueous dispersion which contains an active ingredient mixture comprising at least one chlorotriazine and at least one chloroacetanilide and a novel mixture of surfactants.

Chlorotriazines and chloroacetanilides, processes for their production and their action as herbicides are known from U.S. Pat. No. 2,891,855 and German Offenlegungsschrift No. 2 328 340. Mixtures of these two classes of compound are commercially available in the form of aqueous dispersions. The combinations of active ingredient contained therein differ in the concentration of the individual compounds according to the crop, the nature of the application, climate and the regional weed population.

Each of these active ingredient combinations of chlorotriazines and chloroacetanilides specially adjusted to the particular requirements needs a particular formulation, i.e. especially a different kind of combination of surfactants. The formulation of such active ingredient combinations is further complicated by the fact that the different crystal forms of the same active ingredient that may result from different preparatory methods necessitate another formulation, while otherwise retaining the same ratio of active ingredients to one another. The consequence is that numerous different formulations of the combination of the same active ingredients are necessary and this entails both for the producer and for the end user a considerable risk regarding the safety of applying these compositions. Hence there exists a need to provide a mode of formulation which permits all changes conditional on biological and technological factors in the active ingredient concentration of a flowable concentrated dispersion, without it being necessary to compound the surfactant content of the formulation completely anew.

Accordingly, the present invention has for its object to formulate a flowable herbicidal composition comprising at least one solid disperse phase and a continuous aqueous phase and containing, as active component, a combination of at least one chlorotriazine and at least one chloroanilide, such that said composition contains 10 to 50% by weight of a chlorotriazine of the formula I,

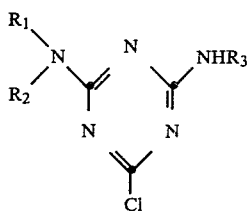

wherein $R_1$ is $C_1$–$C_4$alkyl, $R_2$ is hydrogen or $C_1$–$C_4$alkyl and $R_3$ is $C_3$–$C_4$cycloalkyl, $C_1$–$C_4$alkyl or $C_1$–$C_4$alkyl substituted by methoxy or cyano, or a mixture thereof;

10 to 50% by weight of a chloroacetanilide of the formula II

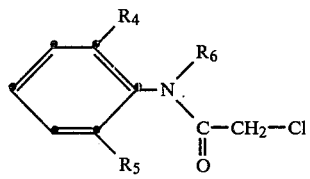

wherein $R_4$ and $R_5$, independently of each other, are methyl or ethyl and $R_6$ is $C_3$–$C_4$alkynyl, $C_1$–$C_3$alkyl or $C_1$–$C_3$alkyl substituted by $C_1$–$C_4$alkoxy, ethoxycarbonyl or pyrazolyl, or a mixture thereof;

1 to 10% by weight of an anionic surfactant of the class of mono- or diphosphoric acid esters of phenol polyglycol ethers, or salts thereof, of the formula III

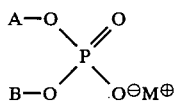

wherein A is a radical of the formula

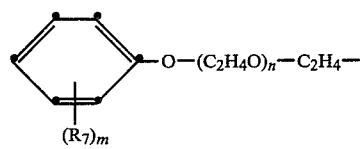

B has the same meaning as A or is hydrogen and $M^\oplus$ is a proton or a sodium cation, a potassium cation or a triethanolammonium cation, n is an integer from 4 to 40, m is an integer from 1 to 4, and $R_7$ is hydrogen, styryl or $C_3$–$C_{10}$alkyl;

0.5 to 10% by weight of a mixture of two non-ionic surfactants of the class of the polyglycol ethers of the formula IV $$R_8\text{—O—}(C_2H_4O)_p\text{—}C_2H_4\text{—OH} \qquad (IV)$$

which differ in the number of glycol units p by at least one, and p is an integer from 2 to 45, and $R_8$ is $C_{12}$–$C_{18}$alkyl, $C_{12}$–$C_{22}$alkanoyl, $C_{12}$–$C_{22}$alkenoyl, $C_{12}$–$C_{22}$alkadienoyl, $C_{12}$–$C_{22}$alkatrienoyl or phenyl which is substituted by $C_5$–$C_8$cycloalkyl or by one to three $C_3$–$C_{10}$alkyl radicals, with the proviso that the mixture component containing the smaller number of glycol units is present in the total composition in an amount of 0.5 to 10% by weight, and the mixture component containing the larger number of glycol units is present in the total composition in an amount of 0 to 9.5% by weight;

0 to 5% by weight of a thickener which is soluble or able to swell in water, and 0 to 25% by weight of a frost protective.

In the definitions of the radicals $R_1$ to $R_6$, alkyl is methyl, ethyl, n-propyl, isopropyl and the butyl isomers. Alkoxy is e.g. methoxy, ethoxy, n-propoxy, isopropoxy and the butoxy isomers. Alkenyl is propargyl, 2-butynyl, 3-butynyl and methylpropargyl. Cycloalkyl radicals are cyclopropyl and cyclobutyl.

Examples of compounds (active ingredients) which can be formulated in the compositions of the invention are:

2-chloro-4,6-bis(ethylamino)-1,3,5-triazine (simazine), 2-chloro-4-ethylamino-6-isopropylamino-1,3,5-triazine (atrazine), 2-(4-chloro-6-ethylamino-1,3,5-triazin-2- ylamino)-2-methylpropionitrile (cyanazine), 2-chloro-4-cyclopropylamino-6-isopropylamino-1,3,5-triazine (cyprazine), 2-tert-butylamino-4-chloro-6-ethylamino-1,3,5-triazine (terbutylazine), 2-chloro-4,6-bis(isopropylamino)-1,3,5-triazine (propazine), 2-chloro-4-isopropylamino-6-(3-methoxypropylamino)-1,3,5-triazine (mesoprazine), 2-chloro-4-tert-butylamino-1,3,5-triazine, 2-chloro-4-ethylamino-6-diethylamino-1,3,5-triazine, 2-chloro-4-ethylamino-6-sec-butylamino-1,3,5-triazine, as well as α-chloro-2'-ethyl-6'-methyl-N-(ethoxymethyl)-acetanilide (acetochlor), 2-chloro-N-(2-methoxyethyl)acet-2',6'-xylidide (dimethachlor), 2-chloro-6'-ethyl-N-(2-methoxy-1-methylethyl)acet-o-toluidide (metolachlor), 2-chloro-2',6'-diethyl-N-(methoxymethyl)acetanilide (alachlor), N-(butoxymethyl)-2-chloro-2',6'-diethylacetanilide (butachlor), α-chloro-2'-ethyl-6'-methyl-N-(propargyl)acetanilide, α-chloro-2'-ethyl-6'-methyl-N-(pyrazol-1-ylmethyl)acetanilide (metazolachlor), and 2-chloro-2',6'-diethyl-N-(2-propoxyethyl)acetanilide (pretilachlor).

Among the triazine compounds, those compounds are preferred which carry only secondary amino groups as substituents, e.g. 2-chloro-4,6-bis(ethylamino)-1,3,5-triazine, 2-chloro-4-ethylamino-6-isopropylamino-1,3,5-triazine, 2-(4-chloro-6-ethylamino-1,3,5-triazin-2-ylamino)-2-methylpropionitrile, 2-tert-butylamino-4-chloro-6-ethylamino-1,3,5-triazine and 2-chloro-4-cyclopropylamino-6-isopropylamino-1,3,5-triazine.

Among the acetanilides, those compounds are preferred which carry an alkoxyalkyl group of altogether at most 5 carbon atoms at the nitrogen atom, e.g. α-chloro-2'-ethyl-6'-methyl-N-(ethoxymethyl)acetanilide, 2-chloro-N-(2-methoxyethyl)acet-2',6'-xylidide, 2-chloro-6'-ethyl-N-(2-methoxy-1-methylethyl)acet-o-toluidide, 2-chloro-2',6'-diethyl-N-(methoxymethyl)acetanilide, N-butoxymethyl)-2-chloro-2',6'-diethylacetanilide, and 2-chloro-2',6'-diethyl-N-(2-propoxyethyl)acetanilide.

Cycloalkyl radicals in the definition of $R_8$ comprise cyclopentyl, cyclohexyl, cycloheptyl and cyclooctyl.

Examples of substituted phenyl groups in the definitions of A or $R_8$ are 4-nonylphenyl; 2,4,6-tributylphenyl; 2,4,6-tristyrylphenyl; 2,4-dinonylphenyl; 2,4,6-tripentylphenyl, 2,4-distyrylphenyl; 4-styrylphenyl; 2,3,4,6-tetrabutylphenyl; 4-decylphenyl; 4-heptylphenyl; 4-pentylphenyl; 2,4-dihexylphenyl; 2,4-dioctylphenyl; 4-octylphenyl; 4-hexylphenyl; 2,4-dipentylphenyl; 2,4,6-tripentylphenyl; 4-cyclohexylphenyl; 4-cyclopentylphenyl and 2,4-dicyclohexylphenyl.

Alkyl radicals of 12 to 18 carbon atoms comprise linear radicals such as n-dodecyl, n-tridecyl, n-tetradecyl, n-pentadecyl, n-hexadecyl, n-heptadecyl and n-octadecyl, and also the isomers thereof with branched chains, e.g. trimethylnonyl, tetramethylnonyl, dimethylundecyl and dipropylhexyl.

Alkanoyl, alkenoyl, alkadienoyl or alkatrienoyl radicals as understood in the definition of $R_8$ are the carboxylic acid radicals which are derived e.g. from the following saturated carboxylic acids: lauric acid ($C_{12}$), myristic acid ($C_{14}$), pentadecylic acid ($C_{15}$), palmitic acid ($C_{16}$), margaric acid ($C_{17}$), stearic acid ($C_{18}$), arachidic acid ($C_{20}$), behenic acid ($C_{22}$) or tuberculostearic acid ($C_{19}$); or from the following simply unsaturated carboxylic acids: lauroleic acid ($C_{12}$), myristoleic acid ($C_{14}$), palmitoleic acid ($C_{16}$), petroselinic acid ($C_{18}$), oleic acid ($C_{18}$), elaidic acid ($C_{18}$), vaccenic acid ($C_{18}$) or erucic acid ($C_{22}$); or from the following carboxylic acids having double to triple unsaturation: linolic acid ($C_{18}$), linolenic acid ($C_{18}$), ricinenic acid ($C_{18}$) and α-eleaostearic acid ($C_{18}$).

The mixtures of non-ionic surfactants of the formula IV normally comprise two surfactants which differ in the number of glycol units by at least one unit. However, in certain borderline cases, which are defined by the structure of the formulated active components, one component of this mixture can be omitted during formulation. The "mixture" then consists of only one non-ionic surfactant.

In order to adjust an optimum degree of viscosity it is frequently necessary to add to the herbicidal composition a thickener which is soluble or able to swell in water. Such suitable thickeners are: polysaccharides of the xantham, alignate, guar or cellulose type, or synthetic macromolecules such as polyethylene glycols, polyvinyl pyrrolidones, polyvinyl alcohols, polyacrylates of swellable structure-forming silicates such as pyrogenic or precipitated silicic acids, bentonites, montmorillonites, hectonites, attapulgites or organic derivatives of the cited structures of aluminium silicates.

In order to maintain the flow properties of the herbicidal composition at low temperatures and to prevent the homogeneous aqueous phase from freezing, frost protectives are normally added to the compositions of the invention. Conventional additives such as ethylene glycol, propylene glycol, glycerol, diethylene glycol, triethylene glycol and tetraethylene glycol and urea are suitable for this purpose.

The formulations contain in general 10 to 50% by weight of a herbicidal chlorotriazine of the formula I or of a mixture of such compounds. Commercial compositions preferably contain 15 to 25% by weight of chlorotriazine. The content of herbicidal chloroacetanilide, or mixture of chloroacetanilides, is also 10 to 50% by weight, preferably 10 to 30% by weight. The combination also contains 1 to 10% by weight, preferably 1 to 3% by weight, of an anionic surfactant of the formula III, 0.5 to 10% by weight of a mixture of two non-ionic surfactants of the formula IV which differ by at least one glycol unit, with the proviso that the non-ionic surfactant with the smaller number of glycol units contained in the total mixture is 0.5 to 10% by weight, preferably 2 to 6% by weight, and the amount of non-ionic surfactant with the greater number of glycol units contained in the total mixture is 0 to 9.5% by weight, preferably 0 to 2% by weight. The flowable herbicidal compositions of the invention optionally contain 0 to 5% by weight of a thickener and 0 to 25% by weight of a frost protective. The preferred amount of frost protective employed depends on the geographical, climatic and seasonal factors of the intended herbicidal application.

The composition of the invention have excellent tolerance to changes in the active component content which are brought about by biological or technical factors. Over a wide range the surfactant component does not need to be varied, or requires only insignificant variation, when increasing or lowering the concentration of a herbicidal compound. Even during prolonged storage of the ready for sale dispersion concentrate, no decomposition or coagulation of the dispersion is observed. Insignificant sedimentation of the solid disperse phase is observed only after very long storage. This sedimentation is normal and can be rectified by simple shaking or stirring. The dispersion is therefore stable.

It is an advantage for the producer that, with the combination of a liquid and a solid active component, both components no longer have to be synchronously emulsified or suspended, but can be prepared and then combined independently of each other in time.

Preferred compositions of the invention comprise the following constituents:

30 to 50% by weight of water,
15 to 25% by weight of a chlorotriazine of the formula I or of a mixture of two such compounds,
10 to 30% by weight of a chloroacetanilide of the formula II,
1 to 4% by weight of an anionic surfactant of the formula III,
2 to 6% by weight of a non-ionic surfactant of the formula VI with (q-r) glycol units, and
0 to 2% by weight of a non-ionic surfactant of the formula IV with q glycol units, where q is an integer from 3 to 45 and r is an integer from 1 to (q-2).

In a further preferred embodiment of the above composition, the chlorotriazine component is atrazine or terbuthylazine or a mixture thereof, the chloroacetanilide is metolachlor, the anionic surfactant is a mixture of a mono- and diphosphate of a tristyryl phenol polyglycol ether or of their triethanolamine salts, or a mixture of a mono- and di-phosphate of a nonyl phenol polyglycol ether or of their potassium or sodium salts, and the non-ionic surfactants are octyl phenol or nonyl phenol polyglycol ethers having 2 to 13 glycol units.

Specific flowable herbicidal formulations comprise the following components:

(α) 23.15% by weight of metolachlor,
23.15% by weight of atrazine,
2.3% by weight of ethylene glycol,
0.2% by weight of silicone oil,
1.7% by weight of a mixture of the triethylamine salts of a mono- and diphosphate of a tristyryl phenol octadecaglycol ether,
3.7% by weight of nonyl phenol hexaglycol ether,
1.1% by weight of nonyl phenol nonaglycol ether,
0.15% by weight of polysaccharide,
0.15% by weight of formaldehyde and water to make up 100%.

(β) 23.15% by weight of metolachlor,
11.58% by weight of atrazine,
11.57% by weight of terbuthylazine,
2.75% by weight of ethylene glycol,
0.25% by weight of silicone oil,
1.40% by weight of a mixture of the triethanolamine salts of a mono- and diphosphate of a tristyryl phenol octadecaglycol ether,
3.70% by weight of nonyl phenol hexaglycol ether,
0.90% by weight of nonyl phenol monoglycol ether,
0.14% by weight of polysaccharide,
0.14% by weight of formaldehyde and water to make up 100%.

(γ) 30.84% by weight of metolachlor,
15.46% by weight of terbuthylazine,
4.60% by weight of ethylene glycol,
0.25% by weight of silicone oil,
1.95% by weight of a mixture of the potassium salts of a mono- and diphosphate of a nonyl phenol hexaglycol ether,
2.80% by weight of nonyl phenol nonoglycol ether,
0.40% by weight of nonyl phenol nonaglycol ether,
0.14% by weight of polysaccharide,
0.14% by weight of formaldehyde, and water to make up 100%.

The following Example will serve to illustrate the invention in more detail.

EXAMPLE 1

Flowable herbicidal compositions α, β and γ, containing atrazine, terbuthylazine and metolachlor respectively, and each of 100 kg, are prepared by:

(a) homogenising the following substances in an agitator vessel by stirring:

|  | Amounts in kg | | |
| --- | --- | --- | --- |
|  | α | β | γ |
| water | 14.50 | 15.75 | 14.40 |
| a mixture of the triethanolamine salts of a mono- and diphosphate of a nonyl phenol hexa- glycol ether | 0.25 | 0.45 | — |
| a mixture of the potassium salts of a mono- and diphosphate of a nonyl phenol hexaglycol ether | — | — | 1.30 |
| nonylphenol hexaglycol ether | 3.47 | 2.80 | 1.85 |
| nonylphenol nonaglycol ether | 0.90 | 0.70 | 0.25 |
| and then, in a uniform stream, adding 96% metolachlor | 24.10 | 24.10 | 32.12 | and stirring the resultant emulsion for 10 minutes;

(b) homogenising the following substances in an agitator vessel by stirring:

|  | Amounts in kg | | |
| --- | --- | --- | --- |
|  | α | β | γ |
| water | 24.65 | 23.8 | 23.75 |
| ethylene glycol | 2.30 | 2.75 | 4.60 |
| a mixture of the triethanolamine salts of a mono- and diphosphate of a tristyryl phenol octadecaglycol ether | 1.45 | 0.95 | — |
| a mixture of potassium salts of a mono- and diphosphate of a nonyl phenol hexaglycol ether | — | — | 0.65 |
| nonylphenol hexaglycol ether | 0.23 | 0.50 | 0.95 |
| nonylphenol nonaglycol ether | 0.20 | 0.20 | 0.15 |
| silicone oil | 0.20 | 0.25 | 0.25 |
| and then stirring in |  |  |  |
| 98% atrazine | 23.62 | 11.80 | — |
| 99% terbuthylazine | — | 11.70 | 15.60 | and homogenising the mixture for 5 to 10 minutes in vacuo and grinding it in a glass bead mill or sand mil to a particle size smaller than 15 μm;

(c) in a further agitator vessel, stirring in 0.14 kg of polysaccharide (xanthum type) in 5.27 kg of water, adding 0.14 kg of 37% formalin, stirring the mixture for 10 minutes and then allowing it to swell for at least 4 hours;

(d) stirring one third of the gel obtained in (c) into the suspension prepared in (b), (e) blending this mixture into the emulsion obtained in (a) and, finally, stirring the remaining two thirds of the gel obtained in (c) into the resultant dispersion until the mixture is homogeneous.

The so prepared compositions contain (α) 23.15% by weight of metolachlor,
23.15% by weight of atrazine,
2.30% by weight of ethylene glycol,
0.20% by weight of silicone oil,
1.70% by weight of a mixture of the triethanolamine salts of a mono- and diphosphate of a tristyryl phenol octadecaglycol ether,
3.70% by weight of nonyl phenol hexaglycol ether,
1.10% by weight of nonyl phenol nonaglycol ether,
0.14% by weight of polysaccharide,
0.14% by weight of formaldehyde and water to make up 100%.

-continued (β) 23.15% by weight of metolachlor,
11.58% by weight of atrazine,
11.57% by weight of terbuthylazine,
2.75% by weight of ethylene glycol,
0.25% by weight of silicone oil,
1.40% by weight of a mixture of triethanolamine salts of a mono- and diphosphate of a tristyryl phenol octadecaglycol ether,
3.70% by weight of nonyl phenol hexaglycol ether,
0.90% by weight of nonyl phenol monoglycol ether
0.14% by weight of polysaccharide,
0.14% by weight of formaldehyde and water to make up 100%.

(γ) 30.84% by weight of metolachlor,
15.46% by weight of terbuthylazine,
4.60% by weight of ethylene glycol,
0.25% by weight of silicone oil,
1.95% by weight of a mixture of potassium salts of a mono- and diphosphate of a nonyl phenol hexaglycol ether,
2.80% by weight of nonyl phenol nonoglycol ether,
0.40% by weight of nonyl phenol nonaglycol ether,
0.14% by weight of polysaccharide,
0.14% by weight of formaldehyde, and water to make up 100%.

The viscosity of the formulations α, β and γ prepared according to Example 1 is 400–800 mPas, the density is 1.08±0.015 g/ml and the pH value is 6.5–7.5.

We claim:

1. A flowable herbicidal composition having at least one solid disperse phase and a continuous aqueous phase comprising
(a) combination of
(i) from 10 to 50% by weight of at least chlorotriazine of the formula:

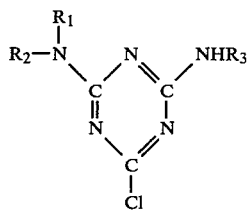

wherein
$R_1$ is alkyl of 1 to 4 carbon atoms,
$R_2$ is hydrogen or alkyl of 1 to 4 carbon atoms, and
$R_3$ is cycloalkyl of 3 or 4 carbon atoms, alkyl of 1 to 4 carbon atoms, or alkyl of 1 to 4 carbon atoms substituted with methoxy or cyano; and
(ii) from 10 to 50% by weight of at least one chloroacetanilide of the formula

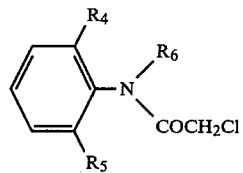

wherein
each of $R_4$ and $R_5$, independently of the other, is methyl or ethyl and
$R_6$ is alkynyl of 3 or 4 carbon atoms, alkyl of 1 to 3 carbon atoms, or alkyl of 1 to 3 carbon atoms substituted with alkoxy of 1 to 4 carbon atoms, ethoxy carbonyl, or pyrazolyl;
(b) a surfactant system consisting essentially of (i) from 1 to 10% by weight of at least one anionic surfactant of the formula:

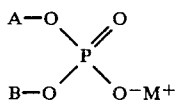

wherein A is

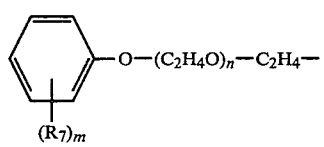

in which
$R_7$ is hydrogen, alkyl of 3 to 10 carbon atoms or styryl;
n is an integer of from 4 to 40 and
m is an integer of from 1 to 4;
B is hydrogen or A; and
M is a proton or a sodium, potassium or triethanolammonium cation; and
(ii) from 0.5 to 10% by weight of at least one non-ionic polyglycol ether surfactant, said surfactant including a compound of the formula:

$R_8O—(C_2H_4O)_p—C_2H_4—OH$ wherein p is an integer from 2 to 44, and
$R_8$ is alkyl of from 12 to 18 carbon atoms, alkanoyl of 12 to 22 carbon atoms, alkadienoyl of 12 to 22 carbon atoms, alkatrienoyl of 12 to 22 atoms, phenyl substituted with cycloalkyl of 5 to 8 carbon atoms or phenyl substituted with from one to three alkyl groups of from 3 to 10 carbon atoms, and
(c) water.

2. A composition according to claim 1 wherein said non-ionic surfactant includes at least two different polyglycol ether surfactants as therein defined.

3. A composition according to claim 1 including up to 5% by weight of a water soluble or water swellable thickener.

4. A composition according to claim 1 including up to 25% of a frost-protective.

* * * * *